US010081797B2

(12) United States Patent
Farrell et al.

(10) Patent No.: US 10,081,797 B2
(45) Date of Patent: Sep. 25, 2018

(54) CAROTENE HYDROXYLASES AND THEIR USE FOR PRODUCING CAROTENOIDS

(71) Applicant: DSM IP ASSETS B.V., Heerlen (NL)

(72) Inventors: Christopher Farrell, Lexington, MA (US); Maria Mayorga, Medford, MA (US); Bastien Chevreux, Rheinfelden (DE)

(73) Assignee: DSM IP ASSETS B.V., Herleen (NL)

( * ) Notice: Subject to any disclaimer, the term of this patent is extended or adjusted under 35 U.S.C. 154(b) by 197 days.

(21) Appl. No.: 14/650,297

(22) PCT Filed: Aug. 27, 2013

(86) PCT No.: PCT/IB2013/056583
§ 371 (c)(1),
(2) Date: Jun. 6, 2015

(87) PCT Pub. No.: WO2014/096990
PCT Pub. Date: Jun. 26, 2014

(65) Prior Publication Data
US 2015/0315550 A1 Nov. 5, 2015

Related U.S. Application Data

(60) Provisional application No. 61/830,273, filed on Jun. 3, 2013.

(30) Foreign Application Priority Data

Dec. 20, 2012 (EP) .................................... 12198352

(51) Int. Cl.
  C12P 23/00 (2006.01)
  C12N 15/52 (2006.01)
  C12N 9/02 (2006.01)
(52) U.S. Cl.
  CPC ............ *C12N 9/0073* (2013.01); *C12P 23/00* (2013.01); *C12Y 114/13129* (2013.01)
(58) Field of Classification Search
  None
  See application file for complete search history.

(56) References Cited

U.S. PATENT DOCUMENTS

| 6,087,152 | A | 7/2000 | Hohmann et al. |
| 7,851,199 | B2 | 12/2010 | Bailey et al. |
| 2012/0156718 | A1 | 6/2012 | Flachmann et al. |

FOREIGN PATENT DOCUMENTS

| EP | 0393690 | 10/1990 |
| EP | 0735137 | 10/1996 |
| EP | 0747483 | 12/1996 |
| WO | WO9113078 | 9/1991 |
| WO | WO9736998 | 10/1997 |

OTHER PUBLICATIONS

Ausubel et al., Current Protocols in Molecular Biology, 1997, (BOOK), Wiley Interscience, New York.
Bolker et al., Tagging pathogenicity genes in Ustilago maydis by restriction enzyme-mediated integration (REMI), Mol Gen Genet, 1995, 547-552, 248.
Bouvier et al., Xanthophyll biosynthesis: molecular and functional characterization of carotenoid hydroxylases from pepper fruits (*Capsicum annuum* L.), Biochimica et Biophysica Acta, 1998, 320-328, 1391.
Brown et al., Stable transformation and regulated expression of an inducible reporter construct in Candida albicans using restriction enzyme-mediated integration, Mol Gen. Genet, 1996, 75-80, 251.
Cunningham et al., Cloning and Functional Analysis of the Beta-Carotene Hydroxylase of *Arabidopsis thaliana*, Journal of Biological Chemistry, 1996, 24349-24352, 271(40).
Database EMBL, Haematococcus pluvialis, Seq 31 from WO2004063359, 2005, Accession No. CQ890446.
Database Geneseq, Haematococcus pluvialis keocarotenoid-related hydroxylase protein, Seq ID No. 16 from WO2005019461, 2005, Accession No. ADY52920.
Database Geneseq, Haematococcus pluvialis ketocarotenoid-related hydroxylase DNA, Seq ID 15, 2005, Accession No. ADY52919.
Database Geneseq, Novel ketocarotenoid preparation method-related protein Seq ID 78, Seq ID 78, 2005, Accession No. ADY52444.
Fraser et al., In Vitro Characterization of Astaxanthin Biosynthetic Enzymes, Journal of Biological Chemistry, 1997, 6128-6135, 272(10).
J. Sambrook, Molcular Cloning, A Laboratory Manual, 1989, Table of contents, Second.
Masamoto et al., Beta-Carotene Hydroxylase Gene from the *Cyanobacterium synechocystic* sp PCC6803, Plant Cell Physiol., 1998, 560-564, 39(5).
Misawa et al., Elucidation of the Erwinia uredovora Carotenoid Biosynthetic Pathway by Functional Analysis of Gene Products Expressed in *Escherichia coli*, Journal of Bacteriology, 1990, 6704-6712, 172(12).
Misawa et al., Structure and Functional Analysis of a Marine Bacterial Carotenoid Biosynthesis Gene Cluster and Astaxanthin Biosynthetic Pathway Proposed at the Gene Level, Journal of Bacteriology, 1995, 6575-6584, 177(22).
Needleman et al., A General Method Applicable to the Search for Similarities in the Amino Acid Sequence of Two Proteins, J. Mol. Biol., 1970, 443-453, 48.
Pasamontes et al., Isolation and characterization of the carotenoid biosynthesis genes of *Flavobacterium* sp. strain R1534, Gene, 1997, 35-41, 185.
Pouwels et al., Elsevier, 1985, (BOOK), Amsterdam-New York, Oxford.
Rice et al., EMBOSS: The European Molecular Biology Open Software Suite, Resource Internet, 2000, 276-277, 16(6).
Schiestl et al., Integration of DNA fragments by illegitimate ercomination in *Saccharomyces cerevisiae*, Proc. Natl. Acad. Sci., 1991, 7585-7589, 88.
Silhavy et al., Experiments with Gene Fusions, (BOOK), 1984, (BOOK).

*Primary Examiner* — Kagnew H Gebreyesus
(74) *Attorney, Agent, or Firm* — Nixon & Vanderhye P.C.

(57) ABSTRACT

The present invention relates to novel hydroxylases, nucleic acid sequences coding therefore, expression constructs and vectors comprising these sequences, microorganisms transformed therewith, processes for the microbiological hydroxylation of isoprenoids, for example processes for converting beta-carotene into beta-cryptoxanthin and zeaxanthin, or canthaxanthin into astaxanthin.

13 Claims, 2 Drawing Sheets
Specification includes a Sequence Listing.

SEQUENCE LISTING

```
<160> NUMBER OF SEQ ID NOS: 8

<210> SEQ ID NO 1
<211> LENGTH: 894
<212> TYPE: DNA
<213> ORGANISM: Haematococcus pluvialis

<400> SEQUENCE: 1
atggctttgt cgaagatgca gccaatgggg gtgcaaggac ggcgcatcgc attgcctcgt       60
gacatctcaa ggcctcagat gccctctcaa aggcagccat tggcccaggt gctacgcgta      120
```

-continued

```
gcagccccag acacagaggc ggtggagtcc tcacgggtgc agccgtctgt cggtgcaggc      180
aatcagcaaa ctgcagacga cgccctccaa cagctcgacc ggtccatcgc tctgcgccgc      240
gctcaacgca aaagggagca gctgacctac caggctgcag ccatagcagc gtccgtgggc      300
atatcaagcc ttgccatcct tgccacctac acgcggtttt caatgcacat acatcagat       360 ggcgagatgc cttggagcga cctcttgggc accctctcac tggtggcagg tggcgcgttt      420
ggcatggaga tgtatgcgcg ttatgcacac aaggccctat ggcatgagtc cccctgggt       480 tggctgctgc acaagagcca ccacactccc cgcaccggac cctttgaagc caatgactta      540
ttcgccatca tcaatggcct gccagccatg ctgctgtgct attatgggtt ctgggagcct      600
ggcatggtcg gcgcctcatg ctttggtgct gggctgggca tcaccctgta cgggatggcg      660
tacatgttca tccatgacgg cctagtccac cggcgctttc ccaccgggcc catctcagac      720
ctgccctaca tgaagcgcct gacagtggcc caccagatcc accacagcgg caagtatgat      780
ggcgcgccct ggggcatgtt cctggggcct caggagctgg aggcaatatc aggtgccaca      840
gaggagctgg accgcttggt ggcagacctg gactggtcaa agcgcagggt gtga           894
```

<210> SEQ ID NO 2
<211> LENGTH: 882
<212> TYPE: DNA
<213> ORGANISM: Haematococcus pluvialis

<400> SEQUENCE: 2

```
atgctgtcga agctgcagtc aatcagcgtc aaggcccgcc gcgttgaact agcccgcgac       60
atcacgcggc ccaaagtctg cctgcatgct cagcggtgct cgttagttcg gctgcgagtg      120
gcagcaccac agacagagga ggcggtggga accgtgcagg ctgccggcgc gggcgatgag      180
cacagcgccg atgtagcact scagcagctt gaccgggcta tcgcagagcg tcgtgcccgg      240
cgcaaacggg agcagctgtc ataccaggct gccgccattg cagcatcaat ggcgtgtca       300 ggcattgcca tcttcgccac ctacctgaga tttgccatgc acatgaccgt gggcggygca      360
gtgccatggg gtgaagtggc tggcactctc ctcttggtgg ttggtggcgc gctcggcatg      420
gagatgtatg cccgctatgc wcacaaagcc atctggcatg agtcgcctct gggctggctg      480
ctgcacaaga gccaccacac acctcgcact ggaccctttg aagccaacga cttgtttgca      540
atcatcaatg gactgcccgc catgctcctg tgtacctttg gcttctggct gcccaacgtc      600
ttgggggcgg cctgctttgg cgcggggctg ggcatcacgc tatacggcat ggcatatatg      660
tttgtacacg atggcctggt gcacaggcgc tttcccaccg ggcccatcgc tggcctgccc      720
tacatgaagc gcctgacagt ggcccaccag cttcaccaca gcggcaagta cggtggcgcg      780
ccctggggca tgttcttggg gccacaggag ctgcagcaca ttccaggtgc tgcggaggag      840
gtggagcgac tagtcctgga actggactgg tcaaagcggt ag                         882
```

<210> SEQ ID NO 3
<211> LENGTH: 297
<212> TYPE: PRT
<213> ORGANISM: Haematococcus pluvialis

<400> SEQUENCE: 3

```
Met Ala Leu Ser Lys Met Gln Pro Met Gly Val Gln Gly Arg Arg Ile
1               5                   10                  15

Ala Leu Pro Arg Asp Ile Ser Arg Pro Gln Met Pro Ser Gln Arg Gln
            20                  25                  30
```

```
Pro Leu Ala Gln Val Leu Arg Val Ala Ala Pro Asp Thr Glu Ala Val
             35                  40                  45

Glu Ser Ser Arg Val Gln Pro Ser Val Gly Ala Gly Asn Gln Gln Thr
 50                  55                  60

Ala Asp Asp Ala Leu Gln Gln Leu Asp Arg Ser Ile Ala Leu Arg Arg
 65                  70                  75                  80

Ala Gln Arg Lys Arg Glu Gln Leu Thr Tyr Gln Ala Ala Ile Ala
                 85                  90                  95

Ala Ser Val Gly Ile Ser Ser Leu Ala Ile Leu Ala Thr Tyr Thr Arg
                100                 105                 110

Phe Ser Met His Ile Thr Ser Asp Gly Glu Met Pro Trp Ser Asp Leu
                115                 120                 125

Leu Gly Thr Leu Ser Leu Val Ala Gly Gly Ala Phe Gly Met Glu Met
            130                 135                 140

Tyr Ala Arg Tyr Ala His Lys Ala Leu Trp His Glu Ser Pro Leu Gly
145                 150                 155                 160

Trp Leu Leu His Lys Ser His Thr Pro Arg Thr Gly Pro Phe Glu
                165                 170                 175

Ala Asn Asp Leu Phe Ala Ile Ile Asn Gly Leu Pro Ala Met Leu Leu
                180                 185                 190

Cys Tyr Tyr Gly Phe Trp Glu Pro Gly Met Val Gly Ala Ser Cys Phe
            195                 200                 205

Gly Ala Gly Leu Gly Ile Thr Leu Tyr Gly Met Ala Tyr Met Phe Ile
            210                 215                 220

His Asp Gly Leu Val His Arg Arg Phe Pro Thr Gly Pro Ile Ser Asp
225                 230                 235                 240

Leu Pro Tyr Met Lys Arg Leu Thr Val Ala His Gln Ile His Ser
                245                 250                 255

Gly Lys Tyr Asp Gly Ala Pro Trp Gly Met Phe Leu Gly Pro Gln Glu
            260                 265                 270

Leu Glu Ala Ile Ser Gly Ala Thr Glu Glu Leu Asp Arg Leu Val Ala
            275                 280                 285

Asp Leu Asp Trp Ser Lys Arg Arg Val
            290                 295

<210> SEQ ID NO 4
<211> LENGTH: 293
<212> TYPE: PRT
<213> ORGANISM: Haematococcus pluvialis

<400> SEQUENCE: 4

Met Leu Ser Lys Leu Gln Ser Ile Ser Val Lys Ala Arg Arg Val Glu
1               5                   10                  15

Leu Ala Arg Asp Ile Thr Arg Pro Lys Val Cys Leu His Ala Gln Arg
                20                  25                  30

Cys Ser Leu Val Arg Leu Arg Val Ala Ala Pro Gln Thr Glu Glu Ala
            35                  40                  45

Val Gly Thr Val Gln Ala Ala Gly Ala Gly Asp Glu His Ser Ala Asp
 50                  55                  60

Val Ala Leu Gln Gln Leu Asp Arg Ala Ile Ala Glu Arg Arg Ala Arg
 65                  70                  75                  80

Arg Lys Arg Glu Gln Leu Ser Tyr Gln Ala Ala Ile Ala Ala Ser
                 85                  90                  95

Ile Gly Val Ser Gly Ile Ala Ile Phe Ala Thr Tyr Leu Arg Phe Ala
                100                 105                 110
```

Met His Met Thr Val Gly Gly Ala Val Pro Trp Gly Glu Val Ala Gly
            115                 120                 125

Thr Leu Leu Val Val Gly Ala Leu Gly Met Glu Met Tyr Ala
        130                 135                 140

Arg Tyr Ala His Lys Ala Ile Trp His Glu Ser Pro Leu Gly Trp Leu
145                 150                 155                 160

Leu His Lys Ser His His Thr Pro Arg Thr Gly Pro Phe Glu Ala Asn
                165                 170                 175

Asp Leu Phe Ala Ile Ile Asn Gly Leu Pro Ala Met Leu Leu Cys Thr
            180                 185                 190

Phe Gly Phe Trp Leu Pro Asn Val Leu Gly Ala Ala Cys Phe Gly Ala
            195                 200                 205

Gly Leu Gly Ile Thr Leu Tyr Gly Met Ala Tyr Met Phe Val His Asp
            210                 215                 220

Gly Leu Val His Arg Arg Phe Pro Thr Gly Pro Ile Ala Gly Leu Pro
225                 230                 235                 240

Tyr Met Lys Arg Leu Thr Val Ala His Gln Leu His His Ser Gly Lys
                245                 250                 255

Tyr Gly Gly Ala Pro Trp Gly Met Phe Leu Gly Pro Gln Glu Leu Gln
            260                 265                 270

His Ile Pro Gly Ala Ala Glu Glu Val Glu Arg Leu Val Leu Glu Leu
            275                 280                 285

Asp Trp Ser Lys Arg
            290

<210> SEQ ID NO 5
<211> LENGTH: 891
<212> TYPE: DNA
<213> ORGANISM: Haematococcus pluvialis

<400> SEQUENCE: 5
atggctctgt ccaagatgca gcccatgggt gtccagggcc gacgaattgc tctcccccga      60
gacatctccc gacccagat gccttccag cgacagcctc tcgcccaggt tctgcgagtt      120 gctgccccg acaccgaggc cgtcgagtct tctcgagtcc agcccctccgt cggtgccggc      180 aaccagcaga ccgccgacga cgccctccag cagctcgacc gatccattgc tctgcgacga      240
gcccagcgaa agcgagagca gctcacctac caggctgctg ccattgccgc ctccgttggt      300
atctcctctc tcgccatcct cgccacctac acccgattct ccatgcacat cacctccgac      360
ggcgagatgc cctggtccga tctcctcggt actctgtctc tcgtcgccgg tggtgccttt      420
ggcatggaga tgtacgcccg atacgcccac aaggctctgt ggcacgagtc tcccctcggc      480
tggctcctcc acaagtccca ccacactccc gaaccggcc ccttcgaggc caacgacctc      540
tttgccatca tcaacggtct gcccgccatg ctcctctgct actacggctt ctgggagccc      600
ggtatggtcg gtgcttcttg tttcggtgct ggcctcggta tcaccctcta cggtatggcc      660
tacatgttca tccacgacgg tctggtccac cgacgattcc ccactggccc catctccgat      720
ctgccctaca tgaagcgact caccgtcgcc caccagatcc accactccgg caagtacgac      780
ggtgctccct ggggtatgtt cctcggcccc caggagctgg aggccatttc cggtgccacc      840
gaggagcttg accgactcgt tgccgatctc gactggtcca agcgacgagt c              891

<210> SEQ ID NO 6
<211> LENGTH: 879
<212> TYPE: DNA

<213> ORGANISM: Haematococcus pluvialis

<400> SEQUENCE: 6

| | | | | | |
|---|---|---|---|---|---|
| atgctctcca | agctccagtc | catctccgtc | aaggcccgac | gtgtcgagct | tgcccgagac | 60 |
| atcacccgac | ccaaggtctg | tctgcacgcc | cagcgatgct | ctctggtccg | actccgagtc | 120 |
| gccgctcccc | agaccgagga | agccgtcggc | accgtccagg | ctgctggtgc | tggtgacgag | 180 |
| cactctgccg | atgttgctct | gcagcagctc | gaccgagcca | ttgccgagcg | acgagcccga | 240 |
| cgaaagcgag | agcagctctc | ttaccaggcc | gccgccatcg | ctgcctccat | tggtgtctcc | 300 |
| ggtattgcca | tctttgccac | ctacctccga | ttcgccatgc | acatgaccgt | tggtggtgcc | 360 |
| gtcccttggg | gtgaggttgc | tggtactctg | ctcctcgttg | tcggtggtgc | tctcggtatg | 420 |
| gagatgtacg | cccgatacgc | ccacaaggcc | atctggcacg | agtctcccct | cggctggctc | 480 |
| ctccacaagt | cccaccacac | tccccgaacc | ggccccttcg | aggccaacga | cctcttcgcc | 540 |
| atcatcaacg | gcctcccgc | catgctgctc | tgtacctttg | gcttctggct | ccccaacgtt | 600 |
| ctcggtgctg | cctgcttcgg | tgccggtctt | ggtatcaccc | tctacggcat | ggcctacatg | 660 |
| ttcgtccacg | acggcctcgt | ccaccgacga | ttccccactg | gccccattgc | tggtctgccc | 720 |
| tacatgaagc | gactcaccgt | cgcccaccag | ctccaccact | ccggcaagta | cggcggtgct | 780 |
| ccctggggta | tgttcctcgg | ccccaggag | ctgcagcaca | tccccggcgc | tgccgaagag | 840 |
| gtcgagcgac | tcgttctcga | gctggactgg | tccaagcgg | | | 879 |

<210> SEQ ID NO 7
<211> LENGTH: 567
<212> TYPE: DNA
<213> ORGANISM: Enterobacter pulveris

<400> SEQUENCE: 7

| | | | | | |
|---|---|---|---|---|---|
| atgcttgtgc | tgtggaatac | gcttatcgtc | atcacgacat | tttgcctgat | ggagattgtg | 60 |
| gcaacgcttg | cccataaata | catcatgcac | ggctggggat | ggggctggca | ccgttcgcac | 120 |
| cacgagccgc | ggcacggctg | gtttgaggtc | aacgatctct | acgcagtggt | gttcgcactg | 180 |
| ctcgccatcg | tgctgatcgc | actgggaaca | gcaggctggt | ggccgctgca | atggcttggc | 240 |
| gcaggcatga | cgctctacgg | tctgttctat | ttcctcgtgc | acgacggtct | ggtgcaccgg | 300 |
| agatggccgt | ttaactacat | tccgcggaga | ggctacctta | gcggcttta | ccaggcacac | 360 |
| cggctgcacc | acgcagtgaa | tggcaaagag | ggttgcgtct | ccttcggttt | tctctacgca | 420 |
| gctaagccgg | aagcacttca | ggcagagctg | cggagacgtc | acggtcggaa | acctaaagca | 480 |
| gacgccgcca | gagcccggcg | ggacggtaaa | cctgtcgcac | agagcgagag | ccgagcacaa | 540 |
| gacctgccgc | cgaaatcggc | agagtaa | | | | 567 |

<210> SEQ ID NO 8
<211> LENGTH: 558
<212> TYPE: DNA
<213> ORGANISM: Enterobacteriaceae DC404

<400> SEQUENCE: 8

| | | | | | |
|---|---|---|---|---|---|
| atgcttgcgt | tgtggaatac | cgggatcgtg | ctactgacta | tcatcatcat | ggaaggggtg | 60 |
| gcaacgttcg | cacacaagta | catcatgcac | ggctgggat | ggggctggca | tcattcgcac | 120 |
| catacccgc | gcaaagggc | gtttgagcgt | aacgatctct | atgcggtggt | gtttgcgcta | 180 |
| ctggccattg | cgctgattta | cgcgggcagc | gaagggtact | ggccgcttca | gtggattggc | 240 |
| gcgggaatga | ccggctacgg | cgtgatctac | tttatcgttc | acgatggtct | tgtccaccag | 300 |

```
cgctggccgt tccgttacgt gccgcgccgc ggctatctgc gccgcctcta catggcacac    360
cggctgcatc acgcggtgcg ggggcgcgaa gggtgcgtct ccttcgggtt tatctacgcc    420
ccaccggtgg acaagctgca ggcggtgctg cgcgaacgta acggcagacc cgccagcgcg    480
ggcgctgcca gaggtgcgga tcgcgcggcg gccagctcgc cttccgggaa gccatcgcct    540
gcttcgcgcc ggaaataa                                                  558
```

CAROTENE HYDROXYLASES AND THEIR USE FOR PRODUCING CAROTENOIDS

CROSS REFERENCE TO RELATED APPLICATIONS

This application is a § 371 National Stage Application of PCT/IB2013/056583, filed Aug. 27, 2013, which claims priority to under 35 U.S.C. § 119(e) to U.S. Provisional Patent Application No. 61/830,273 filed Jun. 3, 2013 and EP 12198352.2, filed Dec. 20, 2012, the entire contents of each of which are hereby incorporated by reference.

BACKGROUND OF THE INVENTION

The present invention relates to novel hydroxylases, nucleic acid sequences coding therefore, expression constructs and vectors comprising these sequences, microorganisms transformed therewith, processes for the microbiological hydroxylation of isoprenoids, for example processes for converting beta-carotene into zeaxanthin or canthaxanthin into astaxanthin.

Carotenoids are organic pigments ranging in color from yellow to red that are naturally produced by certain organisms, including photosynthetic organisms (e.g., plants, algae, cyanobacteria), and some fungi.

Carotenoids such as lutein, zeaxanthin or astaxanthin are important additives in the human and livestock diet as pigmenting substances and precursors of vitamin A derivatives. In addition, carotenoids have a health-promoting action such as enhancing the immune response and, by reason of their antioxidant properties, a cancer-preventing action, which makes their use as nutraceuticals of interest. An economic process for preparing carotenoids and foodstuffs with an increased carotenoid content is therefore of great importance. Particularly economic processes for preparing carotenoids are biotechnological processes which make use of proteins and biosynthesis genes of carotenoid biosynthesis from carotenoid-producing organisms.

Prokaryotic [beta]-carotene hydroxylases which catalyze the enzymatic conversion of [beta]-carotene into zeaxanthin via [beta]-cryptoxanthin, and the genes which encode these proteins are known from the bacteria *Erwinia uredovora* (Misawa et al., J. of Bacteriology 1990, 6704-6712; EP 393690 B1), *Erwinia herbicola* (WO 9113078), *Agrobacterium aurantiacum* (Misawa et al., J. of Bacteriology 1995, 6575-6584; EP 735 137 A1), *Alcaligenes* sp. PC-1 (EP 735 137 A1), *Flavobacterium* sp. strain R1534 (Pasamontes et al., Gene 1997, 185, 35-41; EP 747483 A2) and from the *Cyanobacterium Synechocystis* sp. PCC6803 (Masamoto et al., Plant Cell Physiol. 1998, 39(5), 560-564).

It is also known that the prokaryotic [beta]-carotene hydroxylases from *Agrobacterium aurantiacum*, *Alcaligenes* and *Erwinia uredovora* are additionally able to convert canthaxanthin via adonirubin in astaxanthin (Misawa et al., J. of Bacteriology 1995, 6575-6584; Fraser et al., J. Biol. Chem. 1997, 272, 6128-6135).

From eukaryotic sources, three plant [beta]-carotene hydroxylases are known to catalyze the enzymatic conversion of [beta]-carotene into zeaxanthin via [beta]-cryptoxanthin. The corresponding cDNAs have been isolated from *Arabidopsis thaliana* (Cunningham et al, J. Biol. Chem. 1996, 271, 24349-24352, WO 9736998), and from *Capsicum annuum* L. (Bouvier et al., Biochimica et Biophysica Acta 1998, 1391, 320-328).

Genes of eukaryotic origin have the advantage over prokaryotic genes that they are expressed better in higher transgenic organisms such as plants. Nevertheless, there is still a need to improve and increase the carotenoid productivity for an economic process for preparing carotenoid derivatives or foodstuffs with an increased carotenoid content by incorporating eukaryotic nucleic acids into organisms.

In addition, the appropriate eukaryotic [beta]-carotene hydroxylases in the prior art have the disadvantage that they have only a narrow substrate range so that there is a build-up of metabolic products which cannot be converted by the hydroxylases and may exert an inhibiting effect on the hydroxylases.

SUMMARY OF THE INVENTION

It is an object of the present invention to remedy the described deficiencies of the prior art and to provide a eukaryotic carotene hydroxylase with improved properties.

The inventors have found that the above object is surprisingly achieved by a protein which has an enzymatic activity for hydroxylating isoprenoids, for example [beta]-carotene or canthaxanthin, comprising the amino acid sequence SEQ ID NO:3 or SEQ ID NO:4.

Therefore, the present invention is related to proteins or polypeptides, comprising the amino acid sequence SEQ ID NO:3 or SEQ ID NO:4 or a sequence derived from these sequences by substitution, insertion or deletion of amino acids and having a homology of at least 50% at the amino acid level with the sequence SEQ ID NO:3 or SEQ ID NO:4.

In particular the hydroxylases according to the invention if expressed in a strain selected or able to produce a specific carotenoid as for example zeaxanthin or astaxanthin increase the level of these carotenoids compared to strains not transformed with the gene encoding the protein or polypeptide according to the invention.

The present invention also relates to isolated polynucleotides encoding the polypeptides of the present invention, nucleic acid constructs, recombinant expression vectors, and recombinant host cells comprising the polynucleotides, and to methods of producing the polypeptides.

The present invention also provides improved systems for the biological production of carotenoids. In one preferred example, the invention provides oleaginous fungi (including, for example, yeast) that produce one or more carotenoids. The present invention also provides methods of constructing such yeast and fungi, methods of using such yeast and fungi to produce carotenoids, and methods of preparing carotenoid-containing compositions, such as food or feed additives, or nutritional supplements, using carotenoids produced in such oleaginous yeast or fungi. In particular, the present invention provides systems and methods for generating yeast and fungi containing polynucleotides encoding the polypeptides of the present invention.

Overview of Sequence Listing

Figure 1:
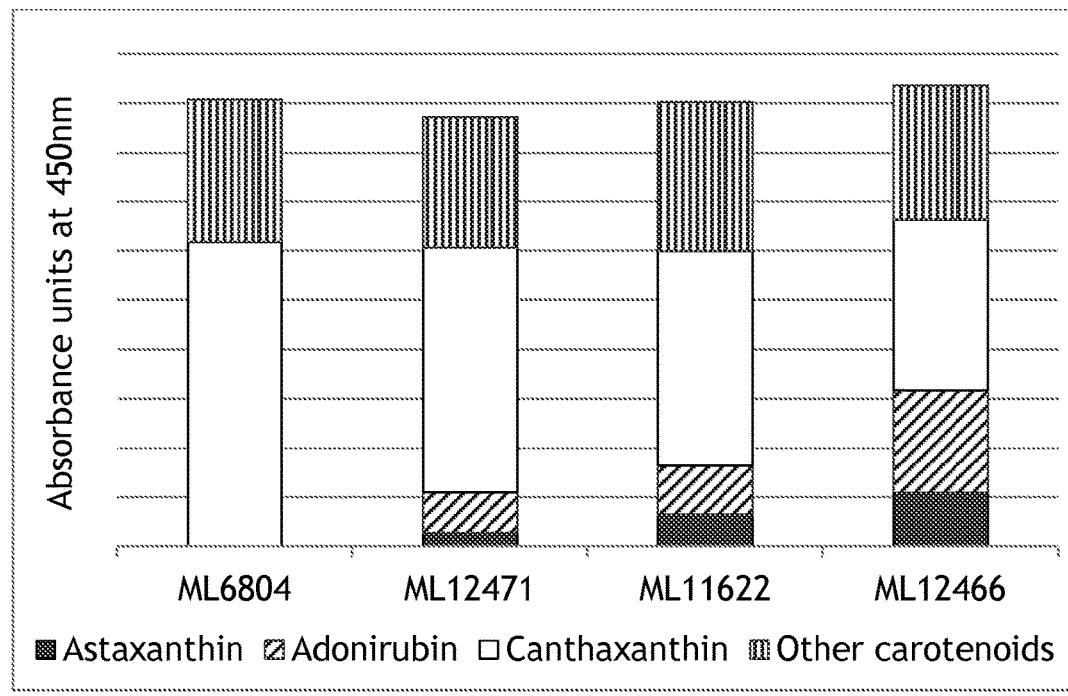
FIG. 1 depicts a representative transformant from each transformation alongside the parent strain ML6804.

SEQ ID NO:1 is the non-optimized DNA sequence of Low Frequency hydroxylase as isolated from *H. pluvialis*.

SEQ ID NO:2 is the non-optimized DNA sequence of Med Frequency hydroxylase as isolated from *H. pluvialis*.

SEQ ID NO:3 is the amino acid sequence as deduced from SEQ ID NO:1.

SEQ ID NO:4 is the amino acid sequence as deduced from SEQ ID NO:2.

SEQ ID NO:5 is the optimized DNA sequence of Low Frequency carotene hydroxylase from *H. pluvialis*.

SEQ ID NO:6 is the optimized DNA sequence of Med Frequency caroene hydroxylase from *H. pluvialis*.

SEQ ID NO:7 is the optimized DNA sequence of the carotene hydroxylase from *Enterobacter pulveris* (Ep).

SEQ ID NO:8 is the optimized DNA sequence of the carotene hydroxylase from Enterobacteriaceae bacterium DC404 (Dc).

Definitions

Isolated polypeptide: The term "isolated polypeptide" means a polypeptide that is modified by the hand of man relative to that polypeptide as found in nature. In one aspect, the polypeptide is at least 1% pure, e.g., at least 5% pure, at least 10% pure, at least 20% pure, at least 40% pure, at least 60% pure, at least 80% pure, and at least 90% pure, as determined by SDS-PAGE.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99% pure, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Fragment: The term "fragment" means a polypeptide having one or more (several) amino acids deleted from the amino and/or carboxyl terminus of a mature polypeptide; wherein the fragment has hydroxylase activity.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" means a polynucleotide that is modified by the hand of man relative to that polynucleotide as found in nature. In one aspect, the isolated polynucleotide is at least 1% pure, e.g., at least 5% pure, at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Variant: The term "variant" means a polypeptide having hydroxylase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

DETAILED DESCRIPTION OF THE INVENTION

Carotene hydroxylases hereinafter mean proteins or polypeptides according to the invention, i.e. proteins which have for example an enzymatic activity for converting [beta]-carotene into zeaxanthin or canthaxanthin into astaxanthin, comprising the amino acid sequence SEQ ID NO:3 or SEQ ID NO:4 or a sequence derived from these sequences by substitution, insertion or deletion of amino acids and having a homology of at least 50% at the amino acid level with the sequence SEQ ID NO:3 or SEQ ID NO:4.

The amino acid sequence depicted in SEQ ID NO:3 is derived from translation of the cDNA sequence depicted in SEQ ID NO:1 and the amino acid sequence depicted in SEQ ID NO:4 is derived from translation of the cDNA sequence depicted in SEQ ID NO:2. Optimized sequences of SEQ ID NO: 1 and 2 are shown in SEQ ID NO: 5 and 6 respectively.

Substitution means replacement of one or more amino acids by one or more amino acids. The replacements are preferably those called conservative, in which the replaced amino acid has a similar property to the original amino acid, for example replacement of Glu by Asp, Gln by Asn, Val by Ile, Leu by Ile, Ser by Thr.

Deletion is the replacement of an amino acid by a direct linkage. Preferred positions for deletions are the termini of the polypeptide and the linkages between the individual protein domains.

Insertions are introductions of amino acids into the polypeptide chain, there formally being replacement of a direct linkage by one or more amino acids.

The homology between two proteins means identity of the amino acids over the entire length of each protein, which is calculated by comparison with the aid of the computer program GAP (UWGCG, University of Wisconsin, Genetic Computer Group, program algorithm of Needleman and Wunsch, J. Mol. Biol. 1970, 48, 443-453), setting the following parameters:
Gap Weight: 12
Length Weight: 4
Average Match: 2.912
Average Mismatch: −2.003

A protein which has a homology of at least 50% at the amino acid level with the sequence SEQ ID NO:3 or SEQ ID NO:4 means a protein which, in comparison of its sequence with the sequence SEQ ID NO:3 or SEQ ID NO:4 using the above program algorithm with the above set of parameters, has an identity of at least 50%, preferably 60%, particularly preferably 70%.

The proteins according to the invention are able to catalyze the conversion of a [beta]-ionone structural element into a 3-hydroxy-[beta]-ionone structural element, such as the conversion of [beta]-carotene into zeaxanthin, [beta]-carotene into [beta]-cryptoxanthin, [beta]-cryptoxanthin into zeaxanthin, echinenone into 3'-hydroxyechinenone, 3-hydroxyechinenone into adonixanthin (4-ketozeaxanthin), [alpha]-carotene into [alpha]-cryptoxanthin or other chemical compounds which have up to 40 C atoms and contain a [beta]-ionone ring into the corresponding 3-hydroxy-[beta]-ionone compounds or the conversion of a 4-keto-[beta]-ionone structural element into a 3-hydroxy-4-keto-[beta]-ionone structural element, such as the conversion of canthaxanthin into astaxanthin, canthaxanthin into phoenicoxanthin (adonirubin), phoenicoxanthin (adonirubin) into astaxanthin, echinenone into 3-hydroxyechinenone, 3'-hydroxyechinenone into adonixanthin (4-ketozeaxanthin) or other chemical compounds which have up to 40 C atoms and contain a 4-keto-[beta]-ionone ring into the corresponding 3-hydroxy-4-keto-[beta]-ionone compounds.

The carotene hydroxylases can be prepared, as described hereinafter, by gene expression of the appropriate nucleic acids which encode these proteins from natural or genetically manipulated organisms.

The invention further relates to a process for the preparation of carotenoids and carotenoid derivatives, which comprises converting a [beta]-ionone structural element into a 3-hydroxy-[beta]-ionone structural element and/or a 4-keto-[beta]-ionone structural element into a 3-hydroxy-4- keto-[beta]-ionone structural element in the presence of the protein according to the invention.

Carotenoids and carotenoid derivatives are for example zeaxanthin, [beta]-cryptoxanthin, 3'-hydroxyechinenone, 3-hydroxyechinenone, adonixanthin (4-ketozeaxanthin), astaxanthin, phoenicoxanthin (adonirubin), [alpha]-cryptoxanthin, [beta]-cryptoxanthin or lutein or derivatives thereof having up to 40 C atoms and containing at least one 3-hydroxy-[beta]-ionone or at least one 3-hydroxy-4-keto-[beta]-ionone structural element in the molecule, such as, for example, 3-hydroxy-6-vinyl-[beta]-ionone, 3-hydroxy-4-keto-6-vinyl-[beta]-ionone, 3-hydroxyretinol, 3-hydroxy-4-ketoretinol, 3-hydroxyretinal, 3-hydroxy-4-ketoretinal, 3-hydroxyretinoic acid or 3-hydroxy-4-ketoretinoic acid.

In the process according to the invention there is conversion in the presence of the proteins according to the invention of a [beta]-ionone structural element into a 3-hydroxy-[beta]-ionone structural element, such as [beta]-carotene into zeaxanthin, [beta]-carotene into [beta]-cryptoxanthin, [beta]-cryptoxanthin into zeaxanthin, echinenone into 3'-hydroxyechinenone, 3-hydroxyechinenone into adonixanthin (4-ketozeaxanthin), [alpha]-carotene into [alpha]-cryptoxanthin or a chemical compound having up to 40 C atoms and containing a [beta]-ionone ring into the corresponding 3-hydroxy-[beta]-ionone compound or a 4-keto-[beta]-ionone structural element into a 3-hydroxy-4-keto-[beta]-ionone structural element, such as canthaxanthin into astaxanthin, canthaxanthin into phoenicoxanthin (adonirubin), phoenicoxanthin (adonirubin) into astaxanthin, echinenone into 3-hydroxyechinenone, 3'-hydroxyechinenone into adonixanthin (4-ketozeaxanthin) or a chemical compound having up to 40 C atoms and containing a 4-keto-[beta]-ionone ring into the corresponding 3-hydroxy-4-keto-[beta]-ionone compound.

The invention also relates to nucleic acid sequences coding for one of the hydroxylases according to the invention. A preferred nucleic acid has the sequence of SEQ ID NO:1 or SEQ ID NO:2 and the sequence of SEQ ID NO: 5 and 6 respectively.

The invention moreover relates to functional analogs of the nucleic acids according to SEQ ID NO:1 and SEQ ID NO:2 and SEQ ID NO: 5 and 6 respectively, obtained by addition, substitution, insertion and/or deletion of individual or multiple nucleotides, which furthermore code for a hydroxylase having the desired specificity.

The invention also encompasses those nucleic acid sequences which comprise so-called silent mutations or which are modified in comparison with a specifically mentioned sequence in accordance with the codon usage of a specific origin or host organism, and naturally occurring variants of such nucleic acid sequences.

The invention also encompasses modifications of the nucleic acid sequences obtained by degeneration of the genetic code (i.e. without any changes in the corresponding amino acid sequence) or conservative nucleotide substitution (i.e. the corresponding amino acid is replaced by another amino acid of the same charge, size, polarity and/or solubility), and sequences modified by nucleotide addition, insertion, inversion or deletion, which sequences encode a hydroxylase according to the invention having a "modified substrate profile", and the corresponding complementary sequences.

The invention furthermore relates to expression constructs comprising a nucleic acid sequence according to the invention under the genetic control of regulatory nucleic acid sequences; and vectors comprising at least one of these expression constructs.

Preferably, the constructs according to the invention encompass a promoter 5'-upstream of the encoding sequence in question and a terminator sequence 3'-downstream, and, optionally, further customary regulatory elements, and, in each case operatively linked with the encoding sequence. Operative linkage is to be understood as meaning the sequential arrangement of promoter, encoding sequence, terminator and, if appropriate, other regulatory elements in such a manner that each of the regulatory elements can fulfill its intended function on expression of the encoding sequence. Examples of operatively linkable sequences are targeting sequences, or else translation enhancers, enhancers, polyadenylation signals and the like. Further regulatory elements encompass selectable markers, amplification signals, replication origins and the like.

In addition to the artificial regulatory sequences, the natural regulatory sequence can still be present upstream of the actual structural gene. If desired, this natural regulation may be switched off by genetic modification, and the expression of the genes may be enhanced or lowered. However, the gene construct may also be simpler in construction, i.e. no additional regulatory signals are inserted upstream of the structural gene and the natural promoter with its regulation is not removed. Instead, the natural regulatory sequence is mutated in such a way that regulation no longer takes place and the gene expression is increased or reduced. One or more copies of the nucleic acid sequences may be present in the gene construct.

Examples of suitable promoters are: cos, tac, trp, tet, trp-tet, lpp, lac, lpp-lac, lacIq, T7, T5, T3, gal, trc, ara, SP6, l-PR or l-PL promoter, which are advantageously employed in Gram-negative bacteria; and Gram-positive promoters amy and SPO2, the yeast promoters ADC1, MFa, Ac, P-60, CYC1, GAPDH, TEF1 or the plant promoters CaMV/35S, SSU, OCS, lib4, usp, STLS1, B33, nos or the ubiquitin or phaseolin promoter. Particular preference is given to using inducible promoters, for example light- and in particular temperature-inducible promoters, such as the PrP1 promoter.

In principle, all natural promoters with their regulatory sequences can be used. In addition, synthetic promoters may also be used in an advantageous fashion.

The abovementioned regulatory sequences are intended to allow the targeted expression of the nucleic acid sequences and of protein expression. Depending on the host organism, this may mean, for example, that the gene is expressed or over expressed only after induction has taken place, or that it is expressed and/or over expressed immediately and/or constitutively.

The regulatory sequences or factors can preferably have a positive effect on expression and in this manner increase or reduce the latter. Thus, an enhancement of the regulatory elements may advantageously take place at the transcriptional level by using strong transcription signals such as promoters and/or "enhancers". In addition, translation may also be enhanced by improving, for example, mRNA stability.

An expression cassette is generated by fusing a suitable promoter with a suitable hydroxylase nucleotide sequence and a terminator signal or polyadenylation signal. To this end, customary recombination and cloning techniques are used as they are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which allows optimal gene expression in the host. Vectors are well known to the skilled worker and can be found, for example, in "Cloning Vectors" (Pouwels P. H. et al., Ed., Elsevier, Amsterdam-New York-Oxford, 1985). Vectors are to be understood as meaning not only plasmids, but all other vectors known to the skilled worker such as, for example, phages, viruses, such as SV40, CMV, baculovirus and adenovirus, transposons, IS elements, plasmids, cosmids, and linear or circular DNA. These vectors can be replicated autonomously in the host organism or chromosomally.

The vectors according to the invention allow the generation of recombinant microorganisms which are transformed, for example, with at least one vector according to the invention and which can be employed for producing the mutants. The above-described recombinant constructs according to the invention are advantageously introduced into a suitable host organism and expressed. It is preferred to use usual cloning and transfection methods known to the skilled worker in order to bring about expression of the abovementioned nucleic acids in the expression system in question. Suitable systems are described, for example, in current protocols in molecular biology, F. Ausubel et al., Ed., Wiley Interscience, New York 1997.

Suitable host organisms are, in principle, all organisms which allow expression of the nucleic acids according to the invention, their allelic variants, and their functional equivalents or derivatives. Preferred initial organisms are those naturally able to synthesize carotenoids. However, initial organisms able to synthesize carotenoids because of the introduction of carotenoid biosynthesis genes are also suitable. Initial organisms mean prokaryotic or eukaryotic organisms such as, for example, microorganisms or plants. Preferred microorganisms are bacteria, yeasts, algae or fungi.

Therefore, the invention further relates to a process for preparing the genetically modified organisms described below, wherein the carotene hydroxylase genes according to the invention are introduced into the genome of the initial organism. By initial organisms are meant the organisms before the genetic modification according to the invention.

The carotene hydroxylase genes according to the invention can in principle be introduced by all methods known to the skilled worker into the initial organisms described below, which are genetically modified thereby.

They are advantageously introduced into the initial organisms or cells thereof by transformation, transfection, electroporation, using the so-called particle gun, or by microinjection.

The skilled worker can find appropriate methods for microorganisms in the textbooks by Sambrook, J. et al. (1989) Molecular cloning: A laboratory manual, Cold Spring Harbor Laboratory Press, by F. M. Ausubel et al. (1994) Current protocols in molecular biology, John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Harbor Laboratory Press or Guthrie et al. Guide to Yeast Genetics and Molecular Biology, Methods in Enzymology, 1994, Academic Press.

Examples of advantageous methods which may be mentioned are those such as the introduction of the DNA by homologous or heterologous recombination, for example using the ura-3 gene, specifically the ura-3 gene from Ashbya, as described in the German Application DE 19801120.2, and/or by the REMI method (="restriction enzyme mediated integration") which is described below.

The REMI technique is based on the cotransformation of a linear DNA construct which has been cut at both ends with the same restriction endonuclease, together with the restriction endonuclease which was used for this restriction of the DNA construct, into an organism. The restriction endonuclease then cuts the genomic DNA of the organism into which the DNA construct has been introduced together with the restriction enzyme. This leads to an activation of the cell's own repair mechanisms. These repair mechanisms repair the strand breaks in the genomic DNA which have been caused by endonuclease, and during this also incorporate with a certain frequency the cotransformed DNA construct into the genome. Ordinarily, the restriction cleavage sites are retained at both ends of the DNA during this.

This technique was described by Bolker et al. (Mol Gen Genet, 248, 1995: 547-552) for the insertion mutagenesis of fungi. The method was used by Von Schiestl and Petes (Proc. Natl. Acad. Sci. USA, 88, 1991: 7585-7589) to find out whether there is heterologous recombination in Saccharomyces. The method has been described by Brown et al. (Mol. Gen. Genet. 251, 1996: 75-80) for the stable transformation and regulated expression of an inducible reporter gene.

It is possible using the REMI method to position the nucleic acid fragments according to the invention or the aforementioned carotene hydroxylase genes according to the invention at transcriptionally active sites in the genome.

It is possible and advantageous to clone the nucleic acids together with at least one reporter gene into a DNA construct, which is introduced into the genome. This reporter gene ought to make detectability easy by a growth, fluorescence, chemo- or bioluminescence assay or by a photometric measurement. Examples which may be mentioned of reporter genes are antibiotic resistance genes, hydrolase genes, fluorescent protein genes, bioluminescence genes, glucosidase genes, the luciferase gene, [beta]-galactosidase gene, gfp gene, lipase gene, esterase gene, peroxidase gene, [beta]-lactamase gene, acetyl-, phospho- or adenyltransferase gene. These genes make it possible easily to measure and quantify the transcription activity and thus the expression of the genes. This means that it is possible to identify sites in the genome which have a productivity differing by up to a factor of 2.

If it is intended to introduce a plurality of genes, such as, for example, further genes of carotenoid biosynthesis, into the organism, they can all be introduced together with a reporter gene in a single vector, or each individual gene with a reporter gene can be introduced in one vector in each case, into the organism, it being possible to introduce the various vectors at the same time or successively. It is also possible to insert gene fragments coding for the respective activities using the REMI techniques.

Restriction enzymes suitable in principle for integrating the carotene hydroxylase genes or nucleic acid constructs according to the invention into the genome of initial organisms are all known to the skilled worker. Restriction enzymes which recognize only 4 base pairs as restriction cleavage site are less preferred because they cut too often in the genome or in the vector to be integrated, and preferred enzymes recognize 6, 7, 8 or more base pairs as cleavage site, such as BamHI, EcoRI, BglII, SphI, SpeI, XbaI, XhoI, NcoI, SalI, ClaI, KpnI, HindIII, SacI, PstI, BpnI, NotI, SrfI or SfiI, to mention only a few of the possible enzymes. It is advantageous if the enzymes used no longer have cleavage sites in the DNA to be introduced; this increases the efficiency of integration. Ordinarily, 5 to 500 U, preferably 10 to 250, particularly preferably 10 to 100 U of the enzymes are used in the REMI mixture. The enzymes are advantageously employed in an aqueous solution which contains substances for osmotic stabilization, such as sugars such as sucrose, trehalose or glucose, polyols such as glycerol or polyethylene glycol, a buffer with an advantageous buffering in the range of pH 5 to 9, preferably 6 to 8, particularly preferably 7 to 8, such as tris, MOPS, HEPES, MES or PIPES and/or substances to stabilize the nucleic acids, such as inorganic or organic salts of Mg, Cu, Co, Fe, Mn or Mo. It is also possible where appropriate for other substances to be present, such as EDTA, EDDA, DTT, [beta]-mercaptoethanol or nuclease inhibitors. However, it is also possible to carry out the REMI technique without these additions.

The process is carried out at a temperature in the range from 5 to 80° C., preferably from 10 to 60° C., particularly preferably from 20 to 40° C. Other known methods for destabilizing cell membranes are suitable for the process, such as, for example, electroporation, fusion with loaded vesicles or destabilization with various alkali metal or alkaline earth metal salts such as lithium, rubidium or calcium salts, with lithium salts being preferred.

The invention further relates to a correspondingly genetically modified organism, with the expression of the carotene hydroxylase genes according to the invention being increased by comparison with a wild type organism in the case where the initial organism contains a carotene hydroxylase gene, or being caused in the case where the initial organism does not contain a carotene hydroxylase gene, by the genetic modification.

A genetically modified organism means an organism in which the carotene hydroxylase genes or nucleic acid constructs according to the invention have been inserted, preferably by one of the methods described above.

The genetically modified organism contains at least one carotene hydroxylase gene according to the invention or at least one nucleic acid construct according to the invention. Depending on the initial organism, the nucleic acid may be present inside or outside the chromosome.

Carotenoid metabolism in the genetically modified organisms is preferably altered by comparison with the wild type.

Preferred organisms are recombinant fungi and yeast. In a particular embodiment, the recombinant fungus is oleaginous in that it can accumulate lipid to at least about 20% of its dry cell weight; and produces at least one carotenoid selected from the group consisting of antheraxanthin, adonirubin, adonixanthin, astaxanthin, canthaxanthin, capsorubrin, β-cryptoxanthin, α-carotene, β,ψ-carotene, δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, a C30 carotenoid, and combinations thereof, and can accumulate the produced carotenoid to at least about 1% of its dry cell weight. Preferably, the recombinant fungus is a member of a genus selected from the group consisting of: *Aspergillus, Blakeslea, Botrytis, Candida, Cercospora, Cryptococcus, Cunninghamella, Fusarium (Gibberella), Kluyveromyces, Lipomyces, Mortierella, Mucor, Neurospora, Penicillium, Phycomyces, Pichia (Hansenula), Puccinia, Pythium, Rhodosporidium, Rhodotorula, Saccharomyces, Sclerotium, Trichoderma, Trichosporon, Xanthophyllomyces (Phaffia)*, and *Yarrowia*, or is of a species selected from the group consisting of: *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvatus, Cunninghamella echinulata, Cunninghamella elegans, Fusarium fujikuroi (Gibberella zeae), Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullulans, Xanthophyllomyces dendrorhous (Phaffia rhodozyma)*, and *Yarrowia lipolytica*.

Of these naturally oleaginous strains, some also naturally produce carotenoids and some do not; these strains may be additionally utilized as a host cell by introduction of carotenoid biosynthesis genes as disclosed in U.S. Pat. No. 7,851,199.

In other embodiments, the present invention provides a method of producing a carotenoid, the method comprising steps of cultivating a fungus under conditions that allow production of the carotenoid; and isolating the produced carotenoid.

Cultivation of the genetically modified organism according to the invention takes place in a manner known per se, such as cultivation of the appropriate wild type, for example in the case of microorganisms in a suitable medium such as, for example, on agar plates or in suspension culture, or in the case of plants in soil or appropriately suitable nutrient media. By harvesting is meant in the case of microorganisms the isolation of the microorganisms, and in the case of plants the cutting off of the plant or, where appropriate, particular plant parts containing the carotenoids. The carotenoids are isolated in a manner known per se, for example by disruption of the organism cells, extraction of the carotenoids and subsequent purification of the carotenoids by chemical or physical separation methods such as extraction or chromatography.

The following examples illustrate the invention.

EXAMPLES

Table 1 below describes certain *Yarrowia lipolytica* strains used in the following exemplification:

TABLE 1

*Yarrowia lipolytica* strains.

| Strain | Genotype | Construction |
|---|---|---|
| ML5252 | MATA erg9-4789::ura3 tef1P-{HMG-tr GGS carB carRP} prototrophic | Classical and standard molecular genetic techniques |
| ML6804 | MATB erg9-4789::ura3 tef1P-{HMG-tr GGS carB carRP crtW} prototrophic | Classical and standard molecular genetic techniques |
| ML9335 | MATA erg9-4789::URA3 tef1P-{HMG-tr GGS carB carRP crtW crtZ-dc} prototrophic | Classical and standard molecular genetic techniques |
| ML9863 | MATB erg9-4789::URA3 tef1P-{HMG-tr GGS carB carRP crtW crtZ-Xa crtZ-Dc} prototrophic | Classical and standard molecular genetic techniques |
| ML11218 | ML9863 crtW-Δ6180 | Targetted disruption with $Hyg^R$ cassette; subsequent marker removal using cre-lox system |
| ML11453 | ML9335 tef1P-carRP/$Hyg^R$ | Untargeted transformation; additional unmarked copies of pre-existing activities may also have been incorporated. |
| ML11584 | ML9863 tef1P-crtZ-Ep/$Nat^R$ | Untargeted transformation; additional unmarked copies of pre-existing activities may also have been incorporated. |
| ML11956 | MATB erg9-4789::ura3 tef1P-{HMG-tr GGS carB carRP crtW crtZ} | ML11453 × ML11584 |
| ML12526 | ML9335 with tef1P-HMG-tr tef1P-carB 3X tef1P-carRP | Untargetted transformations followed by removal of $Hyg^R$ and $Nat^R$ using cre-lox system |

Enterobacteriaceae bacterium DC404 (Dc) (SEQ ID NO:8), or *Flavobacterium* sp. R1534 (Fb) (U.S. Pat. No. 6,087,152). These genes are sometimes but not always associated with auxotrophic markers (URA3, LEU2, URA2, LYS1, ADE1) or a loxP site, remnant of a $Hyg^R$ (hygromycin resistance) or $Nat^R$ (nourseothricin resistance) marker.

TABLE 2

Plasmids

| Plasmid | Backbone | Insert | Oligos or source |
|---|---|---|---|
| pMB6486 | pMB6157 ($Hyg^R$ tef1P-xprT) | crtZ-$Hp^{LF}$ | Synthesized NheI-MluI fragment |
| pMB6487 | pMB6157 ($Hyg^R$ tef1P-xprT) | crtZ-Fb | Synthesized NheI-MluI fragment |
| pMB6056 | pMB6157 ($Hyg^R$ tef1P-xprT) | crtZ-Ep | Synthesized NheI-MluI fragment |

*Yarrowia* strains ML5252, ML6804, ML9863, and ML9335 were constructed by the introduction of heterologous genes under the control of the endogenous TEF1 promoter, coupled with several generations of crossbreeding, starting with ML350 and ATCC201249 as described in U.S. Pat. No. 7,851,199. The GGS gene and the truncated HMG gene ("HMG-tr") were derived from *Yarrowia* sequences corresponding to native geranylgeranyl pyrophosphate synthase and hydroxymethylglutaryl-CoA reductase genes, respectively. The carRP and carB genes were derived from *Mucor circinelloides*, and they encode a bifunctional phytoene synthase/lycopene cyclase and a phytoene dehydrogenase, respectively. The crtW gene was synthesized to encode the carotene ketolase of *Parvularcula bermudensis* (US 2012/0156718).

The crtZ gene was amplified from *Xanthobacter autotrophicus* (Xa) or synthesized to encode the carotene hydroxylase of *Enterobacter pulveris* (Ep) (SEQ ID NO:7), All basic molecular biology and DNA manipulation procedures described herein are generally performed according to Sambrook et al. or Ausubel et al. (Sambrook J, Fritsch E F, Maniatis T (eds). 1989. *Molecular Cloning: A Laboratory Manual*. Cold Spring Harbor Laboratory Press: New York; Ausubel F M, Brent R, Kingston R E, Moore D D, Seidman J G, Smith J A, Struhl K (eds). 1998. *Current Protocols in Molecular Biology*. Wiley: New York).

Example 1a: Production of pMB6486 ($Hyg^R$ tef-crtZ-$Hp^{LF}$), Encoding *H. pluvialis* Carotene Hydroxylase LF A codon optimized carotene hydroxylase (CrtZ-$Hp^{LF}$) ORF sequence was synthesized de novo based on the protein sequence of *H. pluvialis*, using *Y. lipolytica* codon bias as specified in SEQ ID NO:5. This sequence was cleaved using NheI and MluI and ligated to pMB6157 cut with NheI and MluI to produce pMB6486. The resulting encoded CrtZ-$Hp^{LF}$ protein of pMB6486 is specified in SEQ ID NO:3.

Example 1b: Production of pMB6056 (Hyg$^R$ tef-crtZ-Ep), Encoding *E. pulveris* Carotene Hydroxylase A codon optimized carotene hydroxylase (CrtZ-Ep) was synthesized de novo based on the protein sequence of *Enterobacter pulveris*, using *Y. lipolytica* codon bias as specified in SEQ ID NO:7. This sequence was cleaved using NheI and MluI and ligated into pMB6157 cut with NheI and MluI to produce pMB6056.

Example 1c: Production of pMB6487 (Hyg$^R$ tef-crtZ-Fb), Encoding *Flavobacterium* sp. R1534 Carotene Hydroxylase A codon optimized carotene hydroxylase (CrtZ-Fb) was synthesized de novo based on the protein sequence of *Flavobacterium* sp. R1534 as specified in U.S. Pat. No. 6,087,152, using *Y. lipolytica* codon bias. The sequence was cleaved using NheI and MluI and ligated to pMB6157 cut with NheI and MluI to produce pMB6487.

Example 2A: Introduction of Three Carotene Hydroxylase Genes into the *Y. lipolytica* Canthaxanthin Producing Strain ML6804 to Produce Astaxanthin To test the hydroxylating potential of *H. pluvialis* CrtZ and compare it to *Flavobacterium* sp. R1534 CrtZ and *Enterobacter pulveris* CrtZ, strain ML6804 was transformed with three different constructs:
1) a HindIII-XbaI fragment of pMB6487 that harbors the *Flavobacterium* crtZ gene under the control of tef1p and the hygromycin resistance marker Hyg$^R$;
2) a PvuII fragment of pMB6056 harboring the *Enterobacter pulveris* crtZ gene under the control of tef1p and the hygromycin resistance marker Hyg$^R$;
3) a HindIII-XbaI fragment of pMB6486 harboring the *H. pluvialis* crtZ-LF gene under the control of tef1p and the hygromycin resistance marker Hyg$^R$.

Transformants were selected on YPD with 100 mg/L hygromycin after 3-4 days of growth at 30° C. Ten transformants from each construct were grown in shake flasks for 4 days in YPD. All transformants produced astaxanthin. A representative transformant from each transformation is shown in FIG. 1 alongside the parent strain ML6804. Strain ML12471, containing the *Flavobacterium* sp. R1534 crtZ gene, produced 3% astaxanthin and 9% adonixanthin (as a percentage of the total carotenoid). Strain ML11622, containing the *Enterobacter pulveris* crtZ gene, produced 7% astaxanthin and 11% adonixanthin. And strain ML12466, containing the *H. pluvialis* crtZ-LF gene, produced 12% astaxanthin and 22% adonirubin.

Figure 2:
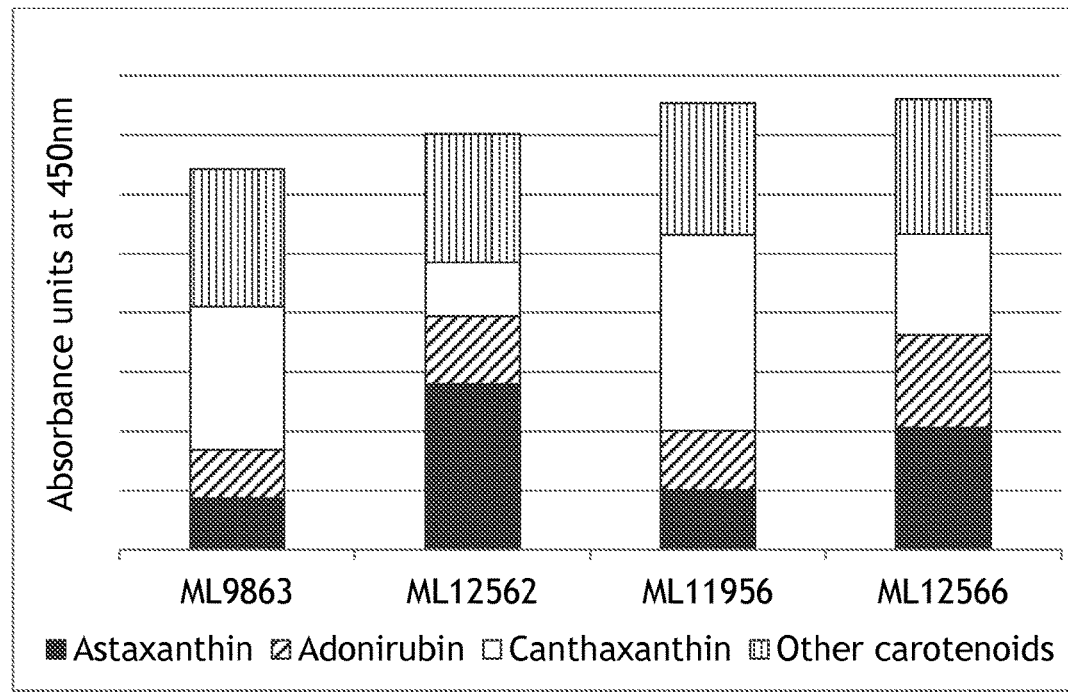
FIG. 2 depicts two representative transformants compared to their parent strains.

Example 2B: Introduction of *H. pluvialis* Carotene Hydroxylase LF into *Y. lipolytica* Astaxanthin Producing Strains to Increase Astaxanthin Purity Strains ML9863 and ML11956 were transformed with a HindIII-XbaI fragment of pMB6486 that harbors the tef1 promoter, the *H. pluvialis* crtZ-LF gene and the selectable marker for hygromycin resistance, Hyg$^R$. Twenty Hyg$^R$ transformants from each strain were chosen that appeared darker than the parents on the transformation plates (YPD with 100 mg/L hygromycin) after 3-4 days of growth at 30° C. Transformants were grown in shake flasks for 4 days in YPD. Two representative transformants are shown in FIG. 2 compared to their parent strains. ML12562 is derived from ML9863 and ML12566 from ML11956. As a percentage of total carotenoid, ML12562 and ML12566 produced 3-fold (40% vs. 13%) and 2-fold (27% vs. 13%) more astaxanthin, respectively, than their parents (FIG. 2).

Figure 3:
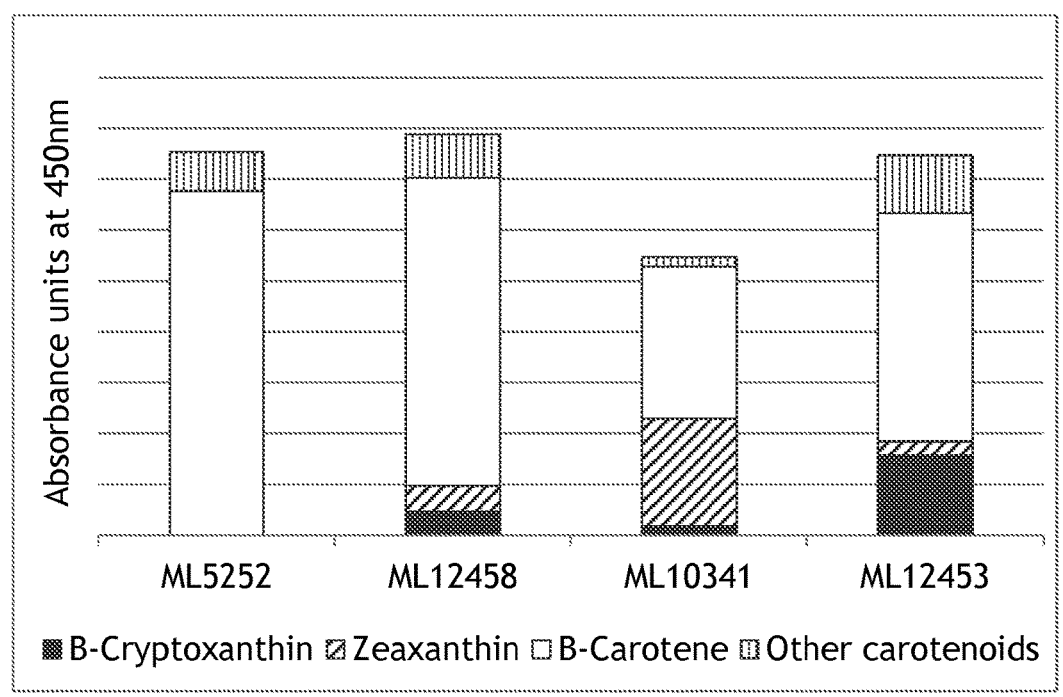
FIG. 3 depicts representative transformants compared to the parent strain ML5252.

Example 2C: Introduction of *H. pluvialis* Hydroxylase LF into a *Y. lipolytica* β-Carotene Producing Strain to Produce β-Cryptoxanthin Strain ML5252 was transformed with three different constructs: 1) a HindIII-XbaI fragment of pMB6487 that harbors the *Flavobacterium* sp. R1534 crtZ gene under the control of tef1p and the hygromycin resistance marker Hyg$^R$; 2) a PvuII fragment of pMB6056 harboring the *Enterobacter pulveris* crtZ gene under the control of tef1p and the hygromycin resistance marker Hyg$^R$; 3) a HindIII-XbaI fragment of pMB6486 harboring the *H. pluvialis* crtZ-LF gene under the control of tef1p and the hygromycin resistance marker Hyg$^R$. Transformants were selected on YPD with 100 mg/L hygromycin after 3-4 days of growth at 30° C. Ten transformants from each construct were grown in shake flasks for 4 days in YPD. All transformants produced zeaxanthin and β-cryptoxanthin. Representative transformants are shown in FIG. 3 compared to the parent strain ML5252. Strain ML12458, containing the *Flavobacterium* crtZ gene, produced 6% β-cryptoxanthin and 6% zeaxanthin (as a percentage of the total carotenoid). Strain ML10341, containing the *Enterobacter pulveris* crtZ gene, produced 3% β-cryptoxanthin and 39% zeaxanthin. And strain ML12453 containing the *H. pluvialis* crtZ-LF gene produced 21% β-cryptoxanthin and 4% zeaxanthin.

Extraction and Quantification of Carotenoid Production by HPLC from *Yarrowia lipolytica* Cells Shake flask testing and carotenoid analysis of generated strains was performed according to the methods described previously in U.S. Pat. No. 7,851,199 B2.

The invention claimed is:

1. An expression vector comprising a nucleic acid molecule that encodes
a polypeptide comprising the amino acid sequence of SEQ ID NO: 3.

2. The expression vector of claim 1, wherein the expression vector encodes a polypeptide that has an enzymatic activity for converting [beta]-carotene into [beta]-cryptoxanthin and/or zeaxanthin, and/or an enzymatic activity for converting canthaxanthin into adonirubin and/or astaxanthin.

3. An isolated nucleic acid comprising the expressing vector of claim 1.

4. The isolated nucleic acid of claim 3, which comprises SEQ ID NO: 1, 2, 5 or 6.

5. A nucleic acid construct or expression vector comprising the sequence of claim 3 or 4 operably linked to one or more (several) control sequences that direct the production of the polypeptide in an expression host cell.

6. A transformed microorganism (host cell) wherein the nucleic acid of claim 3 or 4 construct is expressed.

7. The transformed microorganism of claim 6, whose carotenoid metabolism is different from that of a wild type.

8. The transformed microorganism of claim 7, wherein the said microorganism is an oleaginous strain.

9. The transformed microorganism of claim 8, wherein the said oleaginous strain is a strain of *Yarrowia lipolytica*.

10. A process for producing the transformed microorganism of claim 6, which comprises
introducing a nucleic acid or nucleic acid construct consisting of the sequence depicted in SEQ ID NO:1, 2, 5 or 6 into an organism wherein the nucleic acid or nucleic acid construct is functionally linked to one or more regulation signals.

11. A process for the preparation of carotenoids or carotenoid derivatives, which comprises converting a [beta]-ionone into a 3-hydroxy-[beta]-ionone and/or a 4-keto-[beta]-ionone into a 3-hydroxy-4-keto-[beta] ionone structural element in the presence of the polypeptide encoded by the expression vector of claim 1.

12. A process of claim 11, comprising the steps of:
(a) cultivating a transformed microorganism according to any of claims 6 to 9, under conditions conductive for production of carotenoids; and
(b) recovering the carotenoid or carotenoid derivative from the transformed microorganism.

13. A composition comprising the polypeptide of any of claim 1 or 2.

* * * * *